(12) United States Patent
Norén et al.

(10) Patent No.: US 6,589,184 B2
(45) Date of Patent: Jul. 8, 2003

(54) IMPLANTABLE INTRAVASCULAR PRESSURE DETERMINING DEVICE AND METHOD

(75) Inventors: Kjell Norén, Solna (SE); Seven-Erik Hedberg, Kungsängen (SE); Kenth Nilsson, Åkersberga (SE)

(73) Assignee: St. Jude Medical AB, Järfälla (SE)

( * ) Notice: Subject to any disclaimer, the term of this patent is extended or adjusted under 35 U.S.C. 154(b) by 0 days.

(21) Appl. No.: 10/078,208

(22) Filed: Feb. 19, 2002

(65) Prior Publication Data

US 2003/0078506 A1 Apr. 24, 2003

(30) Foreign Application Priority Data

Aug. 31, 2001 (SE) .............................................. 0102920

(51) Int. Cl.⁷ .................................................. A61B 5/02
(52) U.S. Cl. ........................ 600/486; 600/485; 600/483; 600/481; 600/595
(58) Field of Search .................................. 600/485, 486, 600/488, 483, 484, 481, 595, 587

(56) References Cited

U.S. PATENT DOCUMENTS

| 4,566,456 A | | 1/1986 | Koning et al. | |
|---|---|---|---|---|
| 5,025,791 A | * | 6/1991 | Niwa | .......................... 600/483 |
| 6,026,324 A | | 2/2000 | Carlson | |
| 6,293,915 B1 | * | 9/2001 | Amano et al. | .............. 600/501 |

* cited by examiner

Primary Examiner—Max F. Hindenburg
Assistant Examiner—Navin Natnithithadha
(74) Attorney, Agent, or Firm—Schiff Hardin & Waite

(57) ABSTRACT

In an implantable intravascular pressure determining device and method, a pressure sensor generates a raw pressure signal, an acceleration sensor generates an acceleration signal, and an evaluation unit determines a disturbance pressure signal from the acceleration signal. A processed signal is generated as the difference between the raw pressure signal and the disturbance pressure signal. The processed signal corresponds to intravascular pressure.

14 Claims, 1 Drawing Sheet

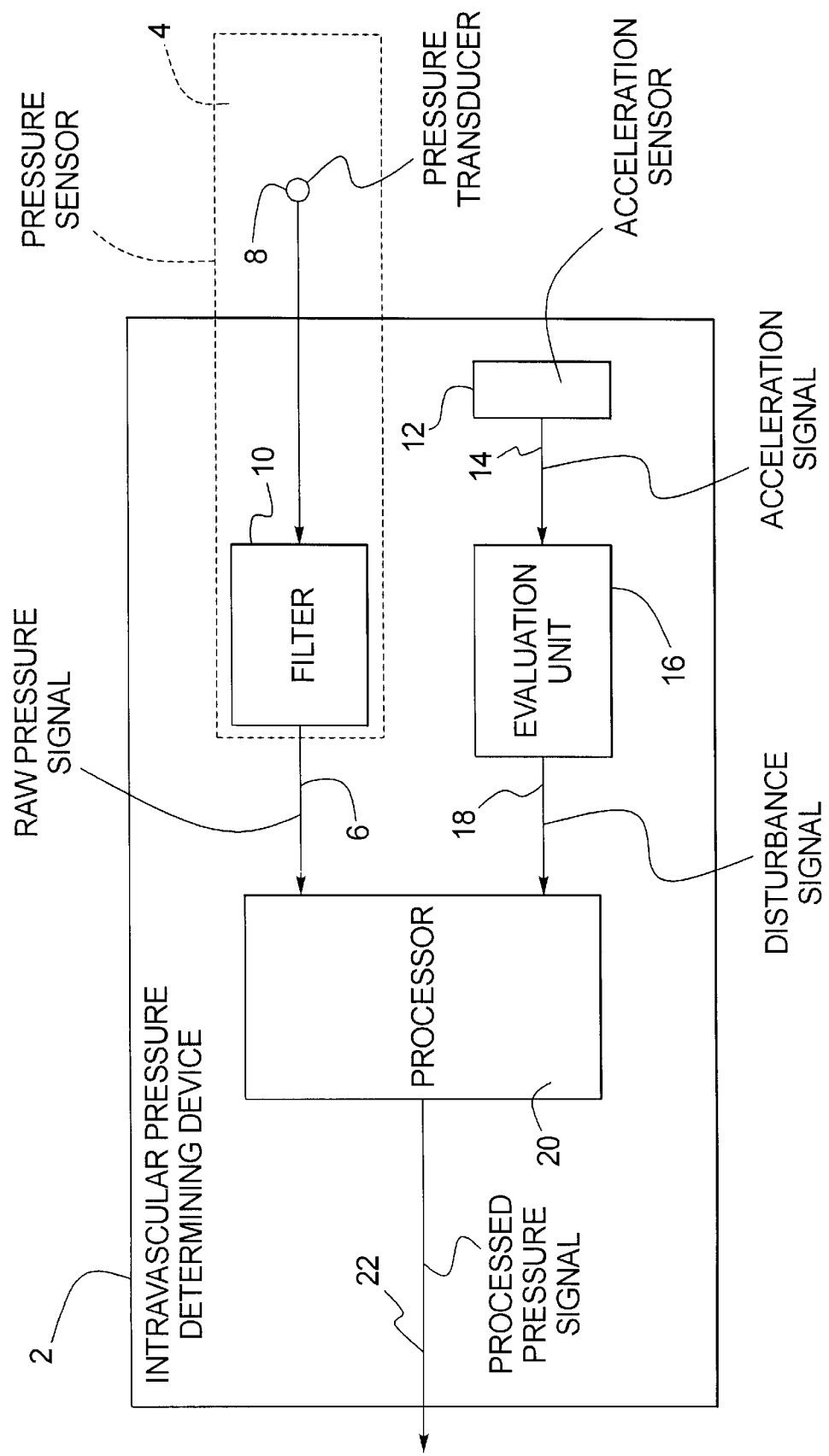

IMPLANTABLE INTRAVASCULAR PRESSURE DETERMINING DEVICE AND METHOD

BACKGROUND OF THE INVENTION

1. Field of the Invention

The present invention relates to an implantable intravascular pressure determining device and method.

2. Description of the Prior Art

A cardiac stimulating apparatus is described in U.S. Pat. No. 6,026,324 that non-intrusively determines a value indicative of hemodynamic pulse pressure from an accelerometer signal obtained by an accelerometer sensor enclosed in an implantable casing of the stimulating apparatus. The accelerometer sensor is electrically coupled to a microprocessor-based controller and the accelerometer transmits a signal to the controller associated with fluid and myocardial accelerations of the patient's heart. A filtering arrangement is coupled to the accelerometer for filtering and conditioning the signal transmitted by the accelerometer to produce a waveform related to a pulse pressure within the patient's heart. In order to remove ancillary information contained in the acceleration signal the signal is transmitted through a series of filters. Thus, the above-referenced United States patent discloses a device capable of non-intrusively (meaning that no sensor needs to be inserted into the heart) determines a waveform related to the pressure and in particular the pulse pressure within a patient's heart.

Measuring pressure inside a heart by inserting a pressure sensor into the heart is well-known in the art. One example is given in the background section of U.S. Pat. No. 6,026,324 where it is referred to U.S. Pat. No. 4,566,456 discloses a device that adjusts the stimulation rate relative to right ventricular systolic pressure. The ventricular systolic pressure is measured by a piezoelectric pressure sensor mounted on an electrode lead inserted into the heart, i.e. an intrusive pressure measurement technique.

In order to obtain accurate and reliable measurements of the intracardial pressure it is often preferred to perform pressure measurements by arranging a pressure sensor inside the heart.

Intracardiac pressure is a highly valuable parameter for estimation of cardiac condition and cardiac pumping efficiency. Technically there is no difficulty in placing a pressure sensor in e.g. the right ventricle of a heart.

Although the pressure sensor may give a correct picture of the pressure at the sensor site, however, the pressure measured in an active patient is a summation of pressures having different origins. Apart from the desired component i.e. the pressure originating from the heart's pumping action, the sensor signal will contain pressure components from other sources such as vibration, external and internal sounds and barometric pressure changes.

In this context, it is relevant to note, that an 11 meter elevation in air gives rise to a pressure change of 1 mm of Hg. Also, it should be noted that the blood column in the body (in the actual case mainly the blood column in the heart) generates pressure changes when the body is exposed to exercise and/or vibrations.

This may be summarized by the following relationship:

$$p = d.h.a \qquad \text{(Equation 1A)}$$

where p is the pressure change, d is the blood density, h is the blood column height and a is the acceleration. It should be noted that in the relationship it is indicated that h and a are vectors.

The same blood column will likewise give rise to pressure changes during body posture changes according to:

$$p = d.h.g \qquad \text{(Equation 1B)}$$

where g is the gravity constant.

External and internal sounds also can make a non-negligible contribution to the pressure signal. Examples of such external sounds are traffic noise and loud music and internal sounds such as coughing, sneezing and snoring.

Taking the above into account, it is fairly difficult to extract the desired signal i.e. the pressure signal emanating solely from the heart's pumping action, from the sensor signal.

For many applications it would be sufficient to measure the cardiac pressure during limited time intervals. One issue is then how to find intervals during which the cardiac pressure signal is the dominating signal contributor.

SUMMARY OF THE INVENTION

An object of the present invention is to extract the cardiac pressure signal from a measured pressure signal obtained by a pressure sensor arranged inside a heart.

Another object of the present invention is to extract the intravascular pressure from a measured pressure signal obtained by a pressure sensor that is arranged in the vascular system of a patient, i.e. in the heart as well as in a blood vessel.

The above object is achieved in accordance with the principles of the present invention in an implantable intravascular pressure determining device, and in a method for determining intravascular pressure, wherein a pressure sensor generates a raw pressure signal, and wherein an acceleration sensor generates an acceleration signal from which a disturbance signal is determined, and wherein a third processed signal is obtained, as the difference between the raw pressure signal the disturbance signal, this processed signal corresponding to the intravascular pressure.

Thus, according to the present invention the accuracy of the pressure measurements obtained by a pressure sensor in the vascular system of a patient is increased. This is generally achieved by correcting the measured pressure by a calculated value representing the disturbing pressure based upon measured values from an acceleration sensor.

DESCRIPTION OF THE DRAWINGS

The FIGURE shows a simplified block-diagram of the implantable intravascular pressure determining device constructed and operating according to the present invention.

DESCRIPTION OF THE PREFERRED EMBODIMENTS

The implantable intravascular pressure determining device 2 shown in the FIGURE has a pressure sensor 4 which generates a raw pressure signal 6. The pressure sensor 4 has a pressure transducer 8 and a filter 10. The pressure transducer 8 is adapted to be positioned in the vascular system of a patient, e.g. in a blood vessel or inside the heart. According to a preferred embodiment of the invention the pressure transducer 8 is an integral part of an electrode lead that is inserted into the heart and is used to apply stimulation pulses to the heart tissue.

The pressure determining device 2 further has an acceleration sensor 12 for generating an acceleration signal 14 and an evaluation unit 16 for determining a control signal 18 from the acceleration signal 14.

The raw pressure signal 6 and the disturbance signal 18 are applied to a processor 20 for generating a processed signal 22 as the difference between the signals 6 and 18, the processed signal 22 representing the intravascular pressure.

The transducer pressure signal generated by the pressure transducer 8 and the acceleration signal 14 need to be filtered. The signal obtained by the pressure transducer 8 is filtered by the filter 10 to obtain the raw pressure signal 6. The filter 10 preferably is a bandpass filter with frequency pass-band in the range between 0.5 and 10 Hz.

The acceleration sensor 12 includes a band-pass filter adapted to filter out the acceleration signal 14. According to a preferred embodiment of the invention it has a similar characteristic as the filter 10.

The evaluation unit 16 and the processor 20 are implemented either by logic circuitry, including amplifying means, or by a combination of a microprocessor and amplifying means.

Those skilled in the art of signal processing are aware of numerous ways of realizing the filtering and among those may be mentioned digitally controlled filters and conventional analog filters.

As briefly discussed above the acceleration sensor 12, which often is incorporated in a pacemaker for activity sensing and rate control, generates the acceleration signal 14, that is a combination of vibration, posture changes, external and internal sounds. This combination of different sources involved may all make contributions to the first intravascular pressure signal 6 that need to be eliminated in order to obtain an intravascular pressure value reflecting the pressure at the measure-site compensated from internal and external disturbances.

The acceleration sensor 12 may be any known implantable accelerometer adapted to generate an acceleration signal. In particular, the accelerometer disclosed in PCT application WO 98/50794 is especially suitable when realizing the present invention. WO-98/50794 discloses an accelerometer including a cantilevered beam with a free end arranged to move. The beam has at least one piezoelectric layer and at least one supporting layer. The free end of the beam is provided with a sensing mass located eccentrically in relation to the longitudinal direction of the beam.

The present invention is applicable to any signal reflecting the pressure in the heart or blood vessel obtained by any type of pressure sensor adapted to be inserted into the heart or into a vessel of a patient. Thus, the pressure sensor 4 to be used in a medical device according to the present invention may in particular be a piezoelectric pressure sensor. Piezoelectric pressure sensors are well-known from the art. For example, U.S. Pat. Nos. 4,566,456 or 5,324,326 disclose a pressure sensor on an integrated circuit chip having a layer of piezoresistive material and a non-conductive base member, with the layer of piezoresistive material being carried by the base member and having a pressure sensing diaphragm area therein exposed to ambient pressure.

Thus, if it is possible to measure pressure during intervals when the output from the accelerometer is zero or at least small, we know that the measured pressure signal consists essentially of the cardiac pressure signal. This is the basic underlying principle of the present invention and also is disclosed in a related patent application having Attorney Docket No. P01,0530 filed simultaneously herewith, the teachings of which are incorporated herein by reference.

The following relationship illustrates the present invention by using the embodiment where the pressure sensor is arranged inside a heart:

$$P_{measured} = P_{disturb} + P_{cardiac}$$

where $P_{measured}$ is the pressure measured (and possibly filtered) by a sensor inside the heart (signal 6), $P_{disturb}$ is the disturbing pressure (signal 18) and $P_{cardiac}$ is the cardiac pressure signal, i.e. the "clean" pressure that is to be determined.

Most of the severely disturbing pressure signals are directly proportional to acceleration according to:

$$P_{disturb} = k \cdot a \qquad \text{(see equations 1A and 1B)}$$

where k is a constant and a is the acceleration. If k is determined, and since a is measured by the accelerometer, then it is possible to determine $P_{disturb}$ that is subtracted from the measured pressure signal resulting in an essentially clean cardiac pressure signal.

There are different ways to determine the constant k.

According to a first preferred embodiment of the present invention, the patient is asked to repeat a physical activity while simultaneously recording the acceleration and the corresponding pressure change. From this measurement the constant k is calculated. The physical activity performed is naturally dependent of the condition of the patient and could be e.g. to stamp with his/her foot on the floor a couple of times, to walk slowly, to kneel, to walk in stairs, etc.

During the physical activity the first pressure signal 6 obtained from the pressure sensor 4 comprises both the intracardiac pressure and pressure originating from the physical activity added together. By comparing the first pressure signal obtained during the physical activity with the first pressure signal obtained when no physical activity is performed the difference represents the disturbing pressure. The constant k is then easily determined by dividing the determined pressure difference with the corresponding acceleration (obtained from the acceleration signal) during the physical activity.

According to a second preferred embodiment of the present invention, the calculation of the constant k can be automatically performed using the information from the acceleration sensor means 12. Selected resting intervals are compared with activity intervals for calculation. This would make the calculation of the constant k self-adaptive. This embodiment is discussed in detail below.

In addition information from a posture sensor could be used to further increase accuracy of the calculation in that the direction of the vectors in the relationships discussed above then easily could be determined.

According to a third preferred embodiment of the present invention the value of k can be determined by obtaining signals from the pressure sensor during moments when there is a reduced heart activity, as during the diastolic interval. During these moments or intervals the dominating pressure in measured pressure signal $P_{measure}$ is $R_{disturb}$, and it would then be possible to obtain a value of the constant k if the acceleration during the same moments or intervals also is determined.

The diastolic interval may be identified in many different ways. One way is to use the intracardiac electrogram (if available) and another way is to study the measured pressure that is low during the diastolic phase of the heart cycle. One way to achieve this may be by having the patient walk around for a couple of minutes.

A number of accelerometer signals will occur during diastole. The values from the pressure sensor and the accelerometer sensor means are then compared and used for obtaining a value of the constant k.

Below follows a detailed description showing two different calculation methods, especially applicable for the above-mentioned second preferred embodiment, of determining the constant k.

According to the first calculation method and using the relation $$P\text{measured} = P\text{disturb} + P\text{cardiac}$$

where $$P\text{disturb} = k*a$$

and thus $$P\text{measured} = k*a + P\text{cardiac}$$

By squaring the relation the instantaneous signal power is obtained:

$$P\text{measured}^2 = k^2*a^2 + 2*k*a*P\text{cardiac} 30\ P\text{cardiac}^2$$

The average signal power (or energy) over a predetermined observation interval can then be calculated.
Let N be the number of samples in the time interval and introduce the symbols $$Pm^2 = \sum_{1}^{N} P\text{measured}^2 / N$$

$$A^2 = \sum_{1}^{N} a^2 / N$$

$$Pc^2 = \sum_{1}^{N} P\text{cardiac}^2 / N$$

for the average of instantaneous power of the measured pressure, the acceleration and the cardiac component, respectively.

$$1/N * \sum_{1}^{N} P\text{measured}^2 = 1/N * \sum_{1}^{N} (k^2 * a^2 + 2 * k * a * P\text{cardiac} + P\text{cardiac}^2)$$

$$Pm^2 = k^2 * 1/N * \sum_{1}^{N} a^2 + 2 * k * \sum_{1}^{N} a * P\text{cardiac}/N + 1/N * \sum_{1}^{N} P\text{cardiac}^2$$

$$Pm^2 = k^2 * A^2 + 2 * k * \sum_{1}^{N} a * P\text{cardiac}/N + Pc^2$$

The mixed term $$2 * k * \sum_{1}^{N} a * P\text{cardiac}/N$$

is small compared to the always positive squared terms over a sufficiency long time interval as the activity creates both positive and negative accelerations.
Thus the basic relation for determining the constant k is:

$$Pm^2 \approx k^2 * A^2 + Pc^2$$

It is convenient to use a measuring interval of 20–30 seconds in order to discriminate from the influence of the patient's respiration. Thus, the pressure and acceleration data measured during a resting interval of 20–30 s is compared to data measured during an activity interval of the same length. A typical sampling frequency of the signals is 100 Hz. This means that the calculation compares the result from data sets of 2000–3000 samples.

Let 1 be the index for data measured during activity and 2 the index for data measured during rest. Then using the relation above:

$$Pm_1^2 = k^2 * A_1^2 + Pc_1^2$$

$$Pm_2^2 = k^2 * 0^2 + Pc_2^2$$

If the exercise is light, then $$Pc_1^2 \approx Pc_2^2$$

for the cardiac component and the relation then becomes:

$$Pm_1^2 = k^2 * A_1^2 + Pm_2^2$$

where $$Pm_1^2 = 1/N * \sum_{1}^{N} P\text{measured}_1^2$$

$$A_1^2 = 1/N * \sum_{1}^{N} a_1^2$$

$$Pm_2^2 = 1/N * \sum_{1}^{N} P\text{measured}_2^2$$

are known parameters and the constant k can then be solved from $$k = \sqrt{\frac{Pm_1^2 - Pm_2^2}{A_1^2}}$$

(It is also apparent that there is no need to use the factor 1/N as this cancels out in the quotient.)
When the value of k is known the estimated instantaneous cardiac component can be calculated as $$\tilde{P}c = P\text{measured} - k*a$$

The estimated $\tilde{P}c$ is to be compared to the real Pcardiac when assessing the accuracy in the calculations.
Some general comments to the above calculations are presented below.

If the value of the calculated k is imaginary, thus $Pm_1^2 < Pm_2^2$, the measured signal during activity is less than during rest, which constitutes changing condition during the measurement. Changing respiration pattern (coughing) can be a cause of this. This is an error condition and the measurement should then be repeated to obtain a correct value.

The method above calculates the absolute value (positive) value of the constant k. The method can however be extended to handle even negative values of k. An easy calculation can be performed to check if the sign of k should be changed. The sign should be changed if the calculated cardiac component $\tilde{P}c$ is larger than the measured pressure amplitude Pmeasured in the interval with the higher activity. This can for instance be done by comparing the average of the absolute values:

(If mean(abs($\tilde{P}c$)) > mean(abs($P$measured)) then $k = -k$, end).

The method works for both dynamic pressure signals with zero average level and also where the dynamic level is superimposed on a constant level. (The method works even for a constant level and the same accounts for the acceleration signal.)

It is convenient to have the same time duration of the calibration intervals, although it is possible to have different lengths.

The calculation of the constant k can be extended even to comparing two activity levels rather than activity and rest. From the relations above:

$$Pm_1^2 = k^2 * A_1^2 + Pc_1^2$$

$$Pm_2^2 = k^2 * A_2^2 + Pc_2^2$$

are the averages of the measured pressure and acceleration at two moderate activity levels.

The cardiac components are approximately equal and the relation of the acceleration components can then be calculated:

$$Pc_1^2 \approx Pc_2^2$$

$$A_1/A_2 = R$$

The average amplitudes for the acceleration components and their relation R is calculated as:

$$A_1 = \sqrt{A_1^2}$$

$$A_2 = \sqrt{A_2^2}$$

$$R = \sqrt{\frac{A_1^2}{A_2^2}}$$

Assuming that $Pm_1$ is measured during the higher activity, the difference $$Pm_1^2 - Pm_2^2 = k^2 * A_1^2 - k^2 * A_2^2 = k^2 * A_1^2 * (1 - 1/R^2)$$

is a solvable expression for the constant k:

$$k = \sqrt{\frac{Pm_1^2 - Pm_2^2}{A_1^2\left(1 - \frac{1}{R^2}\right)}}$$

It can be seen that this is an extension of the previous equation for calculation of k by analyzing the situation with no activity:

$$A_2 \to 0 \Rightarrow R \to \infty \Rightarrow \frac{1}{R^2} \to 0 \Rightarrow k \to \sqrt{\frac{Pm_1^2 - Pm_2^2}{A_1^2}}$$

This is the previous relationship for calculation of k using the resting situation.

Substituting the expression for R into the equation for the constant k gives another expression for the general situation when two activity levels are used for the calibration.

$$k = \sqrt{\frac{Pm_1^2 - Pm_2^2}{A_1^2 - A_2^2}} \qquad A_1^2 > A_2^2$$

The previous equation for estimation of the value of k using two levels of activity or activity/rest used two continuous time segments of equal length.

There is of course no necessity that the two data sets should come from continuous segments. It is instead possible to concatenate measured data from several shorter time windows to form a longer window.

There is also no need to have equal number of samples in the two longer windows. This changes the formulas above in that weighting factors 1/N and 1/M will be added to the formulas where N and M are the number of samples in the two windows.

A test of accuracy of the calculated value of k can be done by investigating the relation of the estimated mixed term to the total energy over the higher activity time interval.

$$\Omega = \frac{2 * k * \sum_1^N \tilde{P}c * a}{\sum_1^N Pmeasured^2} * 100\%$$

If the value of $\Omega$ is a few percent or less the constant k can be considered to be a good estimate while higher values indicate larger errors.

According to the present invention the constant k may be calculated by using a second calculation method based on linear regression using a least mean square (LMS) fit.

As $$P\text{measured} = P\text{disturb} + P\text{cardiac}$$

the constant k can be found by fitting the linear model k*a to the measured data.

This means that the squared error $$\varepsilon = \sum_1^N (Pmeasured - k * a)^2$$

should be minimized.

By setting $$\frac{\partial \varepsilon}{\partial k} = 0$$

the solution for the constant k is $$k = \frac{\sum_1^N Pmeasured * a}{\sum_1^N a^2}$$

The measurements may be performed during one measurement interval having a length of about 30 seconds, or may be performed during a number of different separate intervals.

Applying the above formulas gives the following result for a true k-value of 4.6:

Quotient analyzed by LMS algorithm=4.6197, when using data from a high activity interval.

Quotient analyzed by LMS algorithm=4.6032, when using data from a low activity interval.

Quotient analyzed by LMS algorithm=4.6164, when using data from both activity intervals.

These results should be compared to the result obtained by using the first described calculation method, i.e. 4.6256.

The conclusion is that it is possible to determine an accurate value of the constant k by using either of the two calculation methods described above.

The constant k is preferably calculated not only once but a number of times in order to increase the accuracy of the calculations. Consecutively calculated k-values may then be compared to each other and a k-value may e.g. be accepted only if the difference between a determined k-value and a consecutively determined k-value not exceeds a predetermined small value.

Although modifications and changes may be suggested by those skilled in the art, it is the intention of the inventor to embody within the patent warranted hereon all changes and modifications as reasonably and properly come within the scope of his contribution to the art.

We claim as our invention:

1. An implantable intravascular pressure determining device comprising:

a pressure sensor adapted for interaction with a subject for generating a raw pressure signal;

an acceleration sensor adapted for interaction with said subject for generating an acceleration signal;

an evaluation unit connected to said acceleration sensor for determining a disturbance pressure signal from said acceleration signal; and a processor supplied with said raw pressure signal and said disturbance pressure signal for generating a processed signal, as a difference between said raw pressure signal and said disturbance pressure signal, said processed signal corresponding to intravascular pressure.

2. An implantable intravascular pressure determining device as claimed in claim 1 wherein said evaluation unit determines said disturbance pressure signal by multiplying said acceleration signal by a predetermined constant k.

3. An implantable intravascular pressure determining device as claimed in claim 2 wherein said evaluation unit determines said constant k during a test procedure.

4. An implantable intravascular pressure determining device as claimed in claim 3 wherein said evaluation unit determines said constant k during a test procedure wherein said subject performs physical activity.

5. An implantable intravascular pressure determining device as claimed in claim 4 wherein said evaluation unit determines said constant k by identifying a raw pressure signal difference between said raw pressure signal during a first period when a first level of activity is performed and during a second period when a second level of activity is performed, said second level being lower than said first level, and by dividing said raw pressure signal difference by an acceleration signal difference between respective acceleration signals obtained during said first and second periods, to obtain a quotient which is said constant k.

6. An implantable intravascular pressure determining device as claimed in claim 2 wherein said evaluation unit determines said constant k during a diastolic phase of a heart cycle of said subject.

7. An implantable intravascular pressure determining device as claimed in claim 1 further comprising a heart stimulating device which administers heart stimulating therapy dependent on said intravascular pressure represented by said processed signal.

8. An implantable intravascular pressure determining device as claimed in claim 7 wherein said implantable heart stimulating device has a heart electrode, and wherein said pressure sensor comprises a pressure transducer disposed in said hear electrode which generates a transducer signal, and a filter supplied with said transducer signal which filters said transducer signal to generate said raw pressure signal.

9. A method for determining intravascular pressure, comprising the steps of:

disposing a pressure sensor in a vascular system of a subject and generating a raw pressure signal therefrom;

disposing an acceleration sensor for interaction with a subject and generating an acceleration signal therefrom;

determining a disturbance pressure signal from said acceleration signal; and generating a processed signal as a difference between said raw pressure signal and said disturbance pressure signal, said processed signal corresponding to intravascular pressure.

10. A method as claimed in claim 9 comprising determining said disturbance pressure signal by multiplying said acceleration signal by a predetermined constant k.

11. A method as claimed in claim 10 comprising determining said constant k in a test procedure.

12. A method as claimed in claim 11 comprising subjecting said subject to physical activity during said test procedure.

13. A method as claimed in claim 12 comprising, in said test procedure, subjecting said subject to a first level of activity during a first period and a second level of activity during a second period, said second level being lower than said first level, obtaining said raw pressure signal in each of said first and second periods and determining a raw pressure signal difference between the respective raw pressure signals in said first and second periods, dividing said raw pressure signal difference by an acceleration signal difference between respective acceleration signals obtained during said first and second periods, to obtain a quotient which is said constant k.

14. A method as claimed in claim 10 comprising determining said constant k during a diastolic phase of a heart cycle of said subject.

* * * * *